(12) United States Patent
Rentschler et al.

(10) Patent No.: US 9,581,470 B2
(45) Date of Patent: Feb. 28, 2017

(54) SENSOR DEVICE FOR MEASURING AT LEAST ONE PROPERTY OF A FLUID MEDIUM

(71) Applicant: Robert Bosch GmbH, Suttgart (DE)

(72) Inventors: Simon Rentschler, Stuttgart (DE); Christopher Holzknecht, Stuttgart (DE); Marc Brueck, Bondorf (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/030,269

(22) PCT Filed: Jul. 29, 2014

(86) PCT No.: PCT/EP2014/066280
§ 371 (c)(1),
(2) Date: Apr. 18, 2016

(87) PCT Pub. No.: WO2015/058873
PCT Pub. Date: Apr. 30, 2015

(65) Prior Publication Data
US 2016/0252372 A1    Sep. 1, 2016

(30) Foreign Application Priority Data

Oct. 21, 2013   (DE) .................. 10 2013 221 255

(51) Int. Cl.
*G01D 11/24* (2006.01)
*G01N 25/00* (2006.01)
(Continued)

(52) U.S. Cl.
CPC ......... *G01D 11/245* (2013.01); *G01M 15/102* (2013.01); *G01N 27/4077* (2013.01)

(58) Field of Classification Search
CPC ..................... G01D 11/24; G01N 27/4077
(Continued)

(56) References Cited

U.S. PATENT DOCUMENTS

| | | | |
|---|---|---|---|
| 7,415,877 B2* | 8/2008 | Okumura | G01N 27/407 73/29.05 |
| 2007/0251823 A1* | 11/2007 | Yamada | G01N 27/4077 204/424 |

(Continued)

FOREIGN PATENT DOCUMENTS

| | | | | |
|---|---|---|---|---|
| DE | 102006029631 A1 | 1/2008 | | |
| DE | 102007023158 A1 * | 11/2008 | ......... | G01N 27/4077 |

(Continued)

OTHER PUBLICATIONS

International Search Report for PCT/EP2014/066280, issued on Oct. 1, 2014.

(Continued)

*Primary Examiner* — Lisa Caputo
*Assistant Examiner* — Jamel Williams
(74) *Attorney, Agent, or Firm* — Gerard Messina

(57) ABSTRACT

A sensor device for measuring at least one property of a fluid medium, in particular of an exhaust gas of an internal combustion engine. The sensor device includes at least one protective housing for accommodating at least one sensor element; within the protective housing, at least one flow path being provided that allows flow therethrough by the fluid medium. The flow path has a number of at least three deflection points, where the fluid medium undergoes a directional change about an angle of at least 90°. The sensor device is highly resistant to thermal shock, while, at the same time, the sensor element has a high dynamic response.

12 Claims, 1 Drawing Sheet

(51) Int. Cl.
*G01N 27/407* (2006.01)
*G01M 15/10* (2006.01)

(58) Field of Classification Search
USPC .................................. 73/431, 25.05, 31.05
See application file for complete search history.

(56) References Cited

U.S. PATENT DOCUMENTS

| | | | |
|---|---|---|---|
| 2008/0016948 A1* | 1/2008 | Yamada | G01N 27/4077 73/31.05 |
| 2009/0101502 A1* | 4/2009 | Waldrop | G01N 27/4075 204/424 |
| 2011/0011152 A1* | 1/2011 | Ito | G01N 27/4074 73/23.31 |
| 2011/0126610 A1* | 6/2011 | Sekiya | G01N 27/4077 73/25.05 |

FOREIGN PATENT DOCUMENTS

| | | |
|---|---|---|
| DE | 102007023158 A1 | 11/2008 |
| DE | WO 2008138697 A1 * 11/2008 | ......... G01N 27/4077 |
| EP | 2278316 A1 | 1/2011 |
| EP | 2333534 | 6/2011 |

OTHER PUBLICATIONS

Konrad Reif, "Sensors in the Motor Vehicle. Two-Step Lambda Oxygen Sensors", Springer Wieweg publishers, 2$^{nd}$ edition, 2012, pp. 160-165.

\* cited by examiner

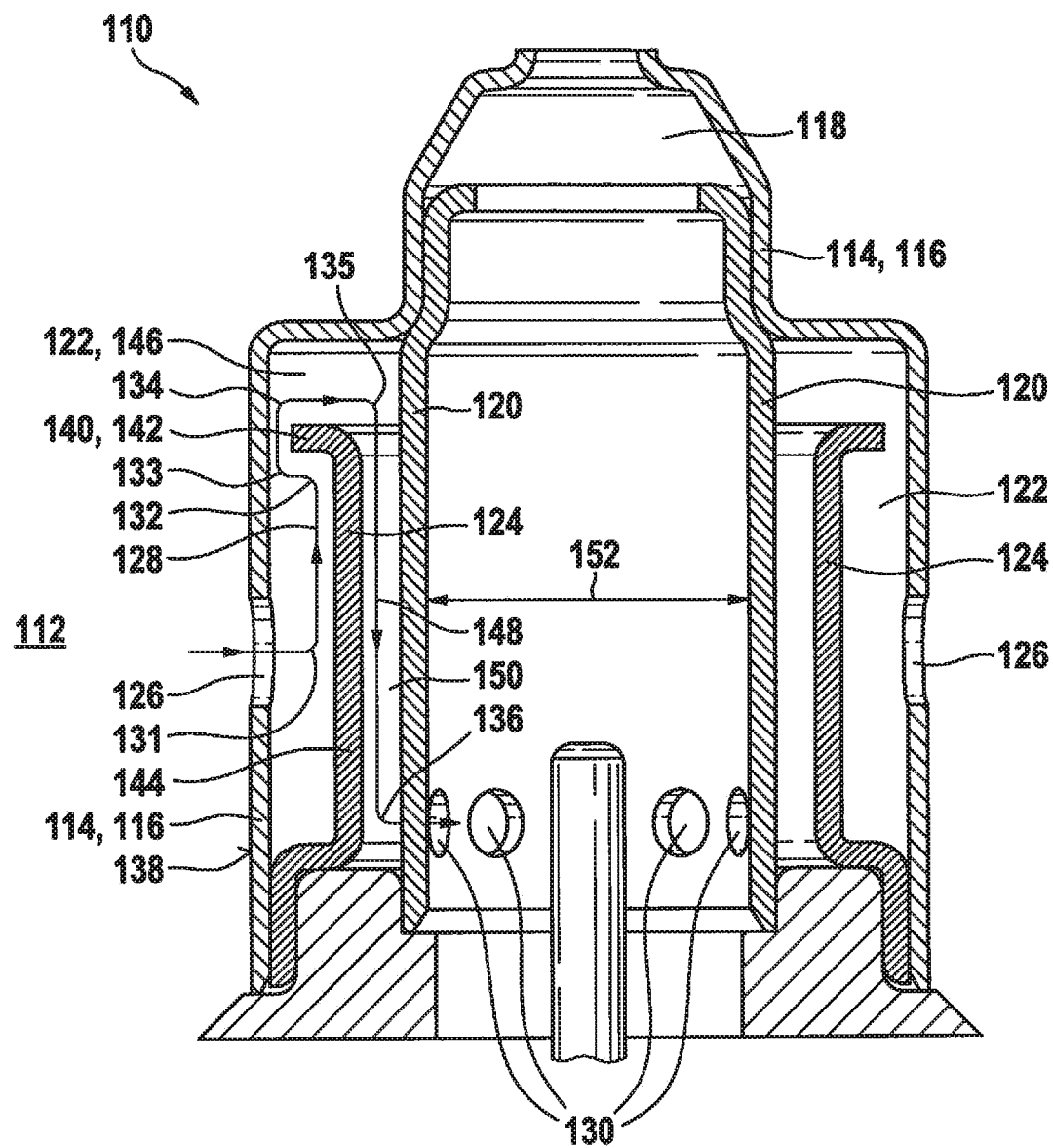

SENSOR DEVICE FOR MEASURING AT LEAST ONE PROPERTY OF A FLUID MEDIUM

BACKGROUND INFORMATION

Sensor devices for measuring at least one property of a fluid medium, preferably of a gas, are available. These include sensor devices having at least one sensor element for measuring at least one parameter of a gas, in particular at least one property of an exhaust gas of a combustion engine, such as the concentration of a constituent of the exhaust gas, in particular the oxygen concentration, the nitrogen oxide concentration, and/or the concentration of gaseous hydrocarbons, for example. Other properties that can be measured using such a sensor device are the particulate matter formation, the temperature and/or the pressure of the fluid medium, for example. In particular, such a sensor device can be a lambda probe. Lambda probes are often used in the exhaust branch of an internal combustion engine, above all for measuring the partial pressure of oxygen in the exhaust gas. Lambda probes are described, for example, in Konrad Reif, *Sensoren im Kraftfahrzeug* (Sensors in the Motor Vehicle), Springer Wieweg publishers, 2nd edition, 2012, pp. 160-165.

At the exhaust gas-side tip thereof, such sensor devices notably have a protective housing that extends into the exhaust stream. The protective housings are used for protection against mechanical stresses that arise during installation, as well as due to particles that occur in the exhaust system, and are used for a controlled guidance of the flow of the fluid medium within the sensor device to the sensor element located therein, as well as for protecting the sensor element from a condensate from the exhaust gas and from an attendant thermal shock to the sensor element. What is commonly known as thermal shock occurs, in particular, when a condensate drop forms from the exhaust stream and precipitates onto the hot, ceramic sensor element, thereby producing local temperature differences on the surface of the sensor element that can result in high, thermally induced stresses in the sensor element that can eventually lead to damage to or even destruction of the sensor element. The protective housing is normally designed to minimize a loading of the sensor device with liquid occurring in the exhaust system, preferably to a volume that is harmless to the sensor element, to a dew point temperature. Moreover, to protect the sensor element from thermal shock, it is preferably also provided with a coating for purposes of thermal insulation and/or fluid binding. In this connection, it is especially advantageous that the coating include a ceramic, in particular an aluminum oxide.

In many cases, however, the requirements for the protective housing are contradictory. In practice, there is, in particular, a conflict of objectives between the requirements for a high level of protection from thermal shock and for a high dynamic response of the sensor device. This especially means that measures performed on the protective housing, that lessen the loading of the sensor element with liquid, often simultaneously reduce the dynamic response of the sensor device. This is due to the fact that, normally, a most rapid possible gas exchange near the sensor element enhances the dynamic response of the sensor device, while the liquid loading of the sensor element is simultaneously hereby increased, generally thereby reducing the protection against thermal shock. In practice, this means that, normally, only one of the two requirements, high dynamic response or high level of protection against thermal shock, can largely be met satisfactorily for a certain selected protective housing.

The protective housing itself may have a one-part or multipart design, a multipart design mostly having an inner housing and an outer housing surrounding the inner housing, between which an intermediate space is formed, in which further protective tubes are possibly located. Protective housings having two or three protective tubes and which, therefore, are also referred to as double or triple protective tube (housings), are used very frequently. A triple protective tube normally provides a better protection against thermal shock than does a double protective tube. However, there are a number of disadvantages inherent in the conventional triple protective tubes. In comparison with a double protective tube, a triple protective tube normally has a longer flow path that the gas stream must travel from the inlet openings at the protective housing to the sensor element. Such a design is, in fact, conducive to protection against thermal shock, but mostly degrades the dynamic response of the sensor device due to the longer flow path. Because of the more stringent requirements placed on the dynamic response, conventional triple protective tubes are no longer suited for such purposes. Moreover, the triple protective tube design, which is customary at present, requires that the inner housing be introduced from the side of a reference air space into the outer housing. Since the diameter of the inner housing must be limited as a result, the limited space in the inner housing necessitates using only those sensor elements that do not have any additional protective coating against thermal shock. However, the lack of a sensor element coating considerably diminishes the liquid volume from the exhaust stream that the sensor element can act upon. In spite of an additional protective tube, this usual triple protective tube configuration ultimately results in the protective action of the entire sensor device against thermal shock being altogether only insignificantly or not enhanced since the sensor element's protection against thermal shock is reduced.

European Patent Application EP 2 333 534 A2 describes a sensor device for measuring at least one property of a fluid medium that is provided with a protective housing for accommodating at least one sensor element. Located within the protective housing is the flow path that is traversable by the fluid medium flow and that extends from the inlet openings in the outer housing across the intermediate space and access openings in the inner housing to the sensor element; within the protective housing, the flow path having two deflection points where the fluid medium undergoes a directional change by an angle of 90°. In addition, at least one wall body is provided within the protective housing along the flow path. It is configured and adapted to absorb heat from the fluid medium that is moved past the wall body at a lowest possible velocity.

SUMMARY

The present invention provides a sensor device for measuring at least one property of a fluid medium, in particular of an exhaust gas of an internal combustion engine, that may at least substantially overcome the conventional limitations and disadvantages. The purpose of such a sensor device is especially to measure at least one property of a fluid medium, preferably one property of the exhaust gas of an internal combustion engine, for example, the oxygen concentration, the nitrogen oxide concentration, and/or of the concentration of gaseous hydrocarbons in the exhaust gas. Measuring other properties of the fluid medium is possible, however. Its design makes the present sensor device especially suited for use at high temperatures, preferably within the range of from 600° C. to 1000° C. However, it is not limited thereto.

An example sensor device according to the present invention includes at least one protective housing that is provided for accommodating at least one sensor element and, for this purpose, at least partially surrounds the sensor element. A protective housing is understood here to be a device that is adapted for protecting the sensor element at least from the usual mechanical and/or chemical stresses that occur during installation of the sensor device and/or during operation thereof. To this end, the protective housing may be at least partially fabricated of a stiff material, in particular of a metal, and/or of an alloy and/or of a ceramic, that do not undergo deformation, especially when the protective housing is fixed in position under usual forces, for instance, usual screw connection forces. In particular, the protective housing may be adapted for outwardly, at least partially surrounding the sensor device and thus for providing at least apart of the sensor device with an outer form. The protective housing may especially be adapted for being completely or partially introduced into the fluid medium, for example, into the exhaust branch of an internal combustion engine.

The protective housing may have a one-part, two-part, three-part or multipart design. One preferred embodiment provides that the protective housing have a two-part design and, accordingly, feature a separate inner housing that may at least partially surround the sensor element, the inner housing itself being able to be at least partially surrounded by an outer housing. This embodiment provides that the inner housing and the outer housing be mounted relative to one another in a way that allows an intermediate space to form between the inner housing and the outer housing. The intermediate space may receive the exhaust gas and preferably take on the shape of an annular gap. One especially preferred embodiment provides that the protective housing have a three-part design; an additional, middle protective housing being introducible into the intermediate space between the inner housing and the outer housing.

Located within the protective housing is a flow path that is traversable by the fluid medium flow. A flow path is understood to be that route that the fluid medium must cover from an entrance into the protective housing to an emergence therefrom before the fluid medium is able to act upon the sensor element subsequently thereto. Besides being defined by a velocity, at which the fluid medium enters into the protective housing and that may be referred to as inlet velocity, this route is generally defined here by a geometric form of an intermediate space within the protective housing. Independently of an actual movement of individual particles and/or molecules in the fluid medium which, on a microscopic scale, may assume a laminar, as well as a turbulent state; on a macroscopic scale, however, the fluid medium always follows an even idealized flow path that may extend along inner walls within the protective housing and interior components possibly located therein. Thus, a configuration of the flow path within the protective housing may be defined by a geometry of the configuration of the protective housing, including the inlet openings located therein, that allow the fluid medium to enter into the intermediate space of the protective housing including the access openings located therein, to allow the fluid medium from the intermediate space to flow to the sensor element and, in some instances, may be defined by the interior components located in the intermediate space.

Accordingly, the present invention provides that the flow path be defined to have at least three deflection points, or at least four deflection points, or at least five deflection points, or at least six deflection points. The fluid medium undergoes a directional change by an angle of at least 90° at each of the at least three deflection points. The directional change at the deflection point is derived here in each particular case from a comparison of the direction of the flow path following an emergence of the fluid medium from the deflection point with the direction of the flow path before the fluid medium enters into the deflection point. One especially preferred embodiment provides that the deflection points be adapted for precipitating liquid contained in the exhaust gas, preferably in the form of condensate drops, onto the inner walls of the protective housing in the area of the deflection points, in particular in response to inertial forces acting on the liquid at the deflection points during the directional change.

In one preferred embodiment, the outer housing may have at least one inlet opening for the fluid medium. In this regard, the outer housing may preferably be at least partially shaped in the form of a cylinder, the cylinder having a curved surface area into which the at least one inlet opening is introduced. In addition, the inner housing may preferably have at least one access opening for the fluid medium emanating from the intermediate space, in particular for feeding the fluid medium to the at least one sensor element. In this preferred embodiment, the flow path extends from the inlet opening through the intermediate space to the access opening, through which the fluid medium ultimately arrives at the sensor element. Provided on the flow path, as explained above, are at least three deflection points, where the fluid medium in each instance undergoes a directional change by an angle of at least 90°.

In another preferred embodiment, an additional, middle protective housing may be introduced into the intermediate space between the inner housing and the outer housing in a way that allows the flow path to preferably extend through an area around the middle protective housing. The flow path through the area around the middle protective housing may be routed in a way that allows at least two of the altogether at least three deflection points, preferably at least four of the at least six deflection points, to be provided in this area. In particular, the middle protective housing may be configured in the intermediate space in such a way and adapted for generating a flow velocity of the fluid medium in the intermediate space that may at least partially exceed the flow velocity of the fluid medium immediately after it traverses the inlet opening. It may become thereby possible to induce an acceleration of the fluid medium at least in individual sections of the flow path in the intermediate space. High flow forces may act on the fluid medium contained in these parts due to a thereby attainable high velocity of flow in individual sections of the flow path, in particular in parts of the intermediate space where two protective housings may be disposed in close mutual proximity or rest closely against each other. Depending on the form of the mentioned parts of the intermediate space, the flow forces occurring here may even exceed the cohesive forces of the individual drops and thereby induce dispersion of the larger drops in the fluid medium into a plurality of smaller drops in each case. Due to the hereby achieved reduction in the medium drop size, drops that still reach the sensor element, in spite of all the protective measures, have a comparatively small volume, thereby making it possible to further diminish the risk of thermal shock occurring on the surface of the sensor element.

Another preferred embodiment provides that the middle protective housing have a fold over which the flow path may extend, the selected geometric design making it possible for the flow path to be thereby provided with at least one, preferably with two, especially with three further deflection points. A fold is understood to be a turned over portion of the middle protective housing that may project into the intermediate space and that, in comparison to the remaining portion, has an angle of less than 180°, preferably of between 60° and 120°, in particular, of about 90°. The directional change induced by the fold in the middle protective housing in a region adjoining the angle may result in an additional precipitation of liquid drops from the fluid medium in the direction of the angle, preferably in response to inertial forces.

Another preferred embodiment provides that the outer housing be adapted to form a hollow space that may be in the form of a hollow dome, for instance, into which the inner housing may be introduced, preferably within which the inner housing may be fixed in position. To allow the gas to enter into the intermediate space of the protective housing, it may be advantageous in this embodiment for the at least one inlet opening for the gas from the exhaust gas space to be configured in the intermediate space in the curved surface area of the cylinder. Moreover, laterally configuring the at least one inlet opening in the curved surface area in this manner may allow the exhaust gas to flow directly into the intermediate space of the protective housing, whereby the flow velocity of the fluid medium may have a value that is higher than that of the related art already immediately upon entry into the intermediate space. As explained above, this higher value may be advantageous, in particular, as the middle drop size in the fluid medium may be thereby further reduced.

The example embodiment of the present sensor device in many ways enhances the insensitivity of the entire sensor device to thermal shock. The routing of the flow path, which is traversable by the flow of the fluid medium, through the protective housing and through at least three deflection points, may improve a precipitation of liquid that may be contained in the fluid medium. Laterally placing the inlet openings for the fluid medium in the curved surface area of the outer housing may increase the flow velocity of the fluid medium in the housing and thus, in particular, improve the dynamic response of the sensor element. Besides accelerating the fluid medium within the protective housing, the increased flow velocity may lead to higher flow forces that may result in the middle drop size being reduced.

It is hereby possible to appreciably minimize the harmfulness of drops, which, in spite of all measures, reach the sensor element. Moreover, routing the flow path over a fold on a still preferably provided middle protective housing may lead to an increased precipitation of drops from the fluid medium.

This preferred type of embodiment of the protective housing provides for gaining space in the interior of the inner housing. This makes it possible to provide the inner housing with a diameter that is selected to provide sufficient space for at least one sensor element having a ceramic coating, preferably a ceramic thermal shock coating, for example, of aluminum oxide. At least one sensor element may thereby be provided with an increased protection against thermal shock. This is in addition to the protection provided by the described embodiment of the protective housing. Thus, in terms of structural design, all of the measures provided work together to thereby attain in all aspects an enhanced insensitivity to and safety against thermal shock for the entire sensor device. Thus, a sensor device in accordance with the present invention may also be used, in particular, for exhaust-gas sensors that may be activated already at the start of an engine.

BRIEF DESCRIPTION OF THE DRAWING

A preferred exemplary embodiment of the present invention is illustrated in the FIG. 1 and will be explained in greater detail in the following description.

FIG. 1 shows a preferred exemplary embodiment of a sensor device according to the present invention having a protective housing in a three-part design in a sectional view.

DETAILED DESCRIPTION OF EXAMPLE EMBODIMENTS

FIG. 1 shows a preferred exemplary embodiment of a sensor device 110 according to the present invention for measuring at least one property of a fluid medium 112. Sensor device 110 includes a protective housing 114 for accommodating at least one sensor element (not shown) that is surrounded by protective housing 114.

In the present, preferred exemplary embodiment, protective housing 114 includes an outer housing 116 that has a hollow space 118 shaped in the form of a dome into which an internal housing 120 is introduced. Outer housing 116 surrounds inner housing 120 in a way that allows an intermediate space 122 to be formed between outer housing 116 and inner housing 120. The present preferred embodiment of protective housing 114 also includes a middle protective housing 124 that is introduced into intermediate space 112 between outer housing 116 and inner housing 120. Other design variants of protective housing 114 for protecting the at least one sensor element of sensor device 110 are possible, however.

Outer housing 116 of protective housing 114 of sensor device 110 has at least one inlet opening 126 through which fluid medium 112 from the exhaust gas space is able to enter into intermediate space 122 between outer housing 116 and inner housing 120. Within protective housing 114, fluid medium 112 is routed on a flow path 128 to an access opening 130 to the interior space (not shown) of inner housing 120 within which the sensor element is located. On the route thereof from inlet opening 126 into intermediate space 122 to access opening 130 from intermediate space 122 into the interior space of inner housing 120, flow path 128 traverses at least three deflection points; in the present exemplary embodiment, six deflection points 131, 132, 133, 134, 135, 136 being provided in succession on flow path 128. Here, "in succession" means that fluid medium 112, once it has passed inlet opening 126, first undergoes a directional change at a first deflection point 131 before being routed to a second deflection point 132 where it undergoes another directional change. Fluid medium 112 subsequently traverses a third deflection point 133, then a fourth deflection point 134, subsequently thereto a fifth deflection point 135, then a sixth deflection point 136, before finally exiting intermediate space 122 through access opening 130 to thereby arrive in the interior space of inner housing 120, to act there upon the sensor element.

At each of these six deflection points 131, 132, 133, 134, 135, 136, fluid medium 112, which moves along flow path 128, undergoes a directional change; in this preferred exemplary embodiment, each time by an angle of 90°. As is readily apparent from FIG. 1, the route of flow path 128 and the six deflection points 131, 132, 133, 134, 135, 136 located therein are defined, in particular, by the specific structural design shape of middle protective housing 124, as well as by the geometric configuration thereof in intermediate space 122 between outer housing 116 and inner housing 120. Thus, first deflection point 131 is produced by the impinging of fluid medium 112, which is delivered to intermediate space 122 from inlet opening 126 located in a curved surface area 138 of outer housing 116, upon middle protective housing 124. Second deflection point 132 and third deflection point 133 are defined by a portion 140 of middle protective housing 124 that is turned over in the manner of a fold and, in one region 142, forms an angle of approximately 90° with remaining portion 144 of middle protective housing 124. Fourth deflection point 134 and fifth deflection point 135 are predefined by a subspace 146 that is not closed, subspace 146 being bounded by outer housing 116, inner housing 120 and turned over portion 140 of middle protective housing 124. Sixth deflection point 136 is defined by the guidance of flow path 128 on a route 148 between inner housing 120 and middle protective housing 124 to access opening 130 into inner housing 120. At each of deflection points 131, 132, 133, 134, 135, 136, the directional change of flow path 128 by an angle of 90° induces a precipitation of liquid from fluid medium 112, preferably in the form of condensate drops. In particular, on route 148 of flow path 128, fluid medium 112 experiences a high flow velocity in narrow gap 150 between inner housing 120 and middle protective housing 124. Comparatively high flow forces thereby act on the drops present in fluid medium 112, dispersing them into droplets. If, in spite of the six deflection points 131, 132, 133, 134, 135, 136 present in this preferred exemplary embodiment, drops nevertheless arrive through access opening 130 to impinge on the sensor element located in inner housing 120, then they at least have a small drop size, thereby lessening the risk of thermal shock on the surface of the sensor element due to the small, supplied individual volumes of these drops.

As is likewise shown in FIG. 1, inner housing 120 is inserted into domed hollow space 118 of outer housing 116, making it possible in the present, preferred variant for inner housing 120 to have an inner diameter 152, whose dimension is selected to allow at least one sensor element to be placed in the interior space of inner housing 120; in which case the sensor element may be additionally provided with a coating to protect against thermal shock. In addition to the embodiment of protective housing 114 described exemplarily in this variant, sensor device 110 according to the present invention is thereby provided with an additional device for protecting against the occurrence of thermal shock.

What is claimed is:

1. A sensor device for measuring at least one property of a fluid medium, comprising:
   at least one protective housing for accommodating at least one sensor element, wherein within the protective housing, at least one flow path is provided that allows flow therethrough by the fluid medium, the flow path having at least three deflection points where the fluid medium undergoes a directional change about an angle of at least 90°;
   wherein an inner housing surrounds the sensor element, the inner housing being at least partially surrounded by an outer housing, the outer housing surrounds the inner housing at least partially in a way that forms an intermediate space, the outer housing having at least one inlet opening for the fluid medium, the inner housing having at least one access opening for the fluid medium from the intermediate space, the flow path extending from the inlet opening across the intermediate space to the access opening;
   wherein the outer housing is at least partially present in the form of a cylinder that is designed to include a curved surface area, the inlet opening being located in the curved surface area;
   wherein the outer housing forms a hollow space into which the inner housing is introduced in a fixed form;
   wherein a middle protective housing is positioned in the intermediate space between the outer housing and the inner housing, the flow path extends in the intermediate space through a region around the middle protective housing, and at least two of the deflection points is present in the region; and
   wherein the middle protective housing is spaced from the inner housing so that the middle protective housing does not directly contact the inner housing.

2. The sensor device as recited in claim 1, wherein the fluid medium is an exhaust gas of an internal combustion engine.

3. The sensor device as recited in claim 1, wherein the number of deflection points in the flow path is at least four.

4. The sensor device as recited in claim 3, wherein the number of deflection points in the flow path is at least five.

5. The sensor device as recited in claim 4, wherein the number of deflection points in the flow path is at least six.

6. The sensor device as recited in claim 1, wherein the deflection points are adapted for precipitating liquid contained in the fluid medium from the fluid medium.

7. The sensor device as recited in claim 1, wherein the middle protective housing is configured in the intermediate space in a way that enables the fluid medium to accelerate on the flow path in the intermediate space.

8. The sensor device as recited in claim 1, wherein the middle protective housing has a turned over portion that projects into the intermediate space and has a remaining portion , the turned over portion having an angle of less than 180° relative to the remaining portion, and wherein the flow path is routed through a region adjacent to the angle, the region having at least two of the deflection points.

9. The sensor device as recited in claim 8, wherein the turned over portion has an angle of between 60° and 120° relative to the remaining portion.

10. The sensor device as recited in claim 9, wherein the turned over portion has an angle of 90°, relative to the remaining portion.

11. The sensor device as recited in claim 1, wherein the sensor element has a ceramic coating, in particular with a thermal shock coating.

12. The sensor device as recited in claim 11, wherein the ceramic coating is a thermal shock coating.

* * * * *